United States Patent [19]

Park et al.

[11] Patent Number: 5,145,644
[45] Date of Patent: Sep. 8, 1992

[54] HYDROGEN PEROXIDE DESTROYING COMPOSITIONS AND METHODS OF MAKING AND USING SAME

[75] Inventors: John Y. Park, Santa Ana; James N. Cook, Mission Viejo, both of Calif.

[73] Assignee: Allergan, Inc., Irvine, Calif.

[21] Appl. No.: 631,621

[22] Filed: Dec. 20, 1990

[51] Int. Cl.$^5$ .................. A61L 2/00; A61K 33/40; A01N 25/00; A01N 37/50
[52] U.S. Cl. .................... 422/28; 422/30; 252/106; 514/840; 424/78.04; 424/94.4; 424/616; 424/468; 427/3
[58] Field of Search .............. 422/28, 30; 252/106; 134/26, 42; 514/839, 840; 424/616, 477, 429, 480, 482, 468, 94.4, 78.04; 427/3

[56] References Cited

U.S. PATENT DOCUMENTS

| Re. 32,672 | 5/1988 | Huth et al. ............... 252/95 |
| 3,910,296 | 10/1975 | Karageozian et al. ........ 134/2 |
| 3,912,451 | 10/1975 | Gaglia Jr. ................ 422/30 |
| 4,499,077 | 2/1985 | Stockel et al. ............ 424/661 |
| 4,557,925 | 12/1985 | Lindahl et al. ............ 424/482 |
| 4,568,517 | 2/1986 | Kaspar et al. ............. 422/30 |
| 4,654,208 | 3/1987 | Stockel et al. ............ 424/78 |
| 4,767,559 | 8/1988 | Kruse et al. .............. 252/106 |
| 4,775,424 | 10/1988 | Wisotzki et al. ........... 134/42 |
| 5,011,661 | 4/1991 | Schäfer et al. ............ 422/30 |

FOREIGN PATENT DOCUMENTS

| 0082798 | 6/1983 | European Pat. Off. . |
| 0147100 | 3/1985 | European Pat. Off. . |
| 0139994 | 5/1985 | European Pat. Off. ........ 422/30 |
| 0209071 | 1/1987 | European Pat. Off. . |
| 0255041A1 | 5/1988 | European Pat. Off. . |
| 0278224 | 8/1988 | European Pat. Off. . |
| 3626082A1 | 11/1988 | Fed. Rep. of Germany . |
| WO8605695 | 10/1986 | PCT Int'l Appl. . |
| 2139260A | 5/1984 | United Kingdom . |
| 2151039A | 12/1984 | United Kingdom . |
| 2173017A | 3/1986 | United Kingdom . |

OTHER PUBLICATIONS

Chemical Selects Abstract Controlled Release Technology Issue 2, 1987.
Eudragit L Data Sheet.

*Primary Examiner*—Robert J. Warden
*Assistant Examiner*—T. A. Trembley
*Attorney, Agent, or Firm*—Frank J. Uxa, Jr.; Gordon L. Peterson

[57] ABSTRACT

Compostions, and method useful for making such compositions and for using such compositions, which are useful to destroy hydrogen peroxide in a liquid aqueous medium, such as that used to disinfect contact lenses, are disclosed. The composition comprises at least one item containing a hydrogen peroxide destroying component, e.g., catalase, effective when released in a liquid aqueous medium to destroy or cause the destruction of hydrogen peroxide present in the liquid aqueous medium, and a barrier coating located on the at least one item and acting to substantially prevent the release of the hydrogen peroxide destroying component for a period of time after the composition is initially contacted with a hydrogen peroxide-containing liquid aqueous medium. The barrier coating comprises a water soluble coating component, e.g., hydroxypropylmethyl cellulose, and is formed by a method which comprises applying a mixture comprising water, a ketone and the water soluble coating component to produce at least one precoated item; and removing water and ketone from the precoated item or items. In a preferred embodiment, the composition includes a cleaning enzyme to remove debris from the contact lens, in particular at the same time the lens is being disinfected.

30 Claims, No Drawings

HYDROGEN PEROXIDE DESTROYING COMPOSITIONS AND METHODS OF MAKING AND USING SAME

BACKGROUND OF THE INVENTION

This invention relates to hydrogen peroxide destroying compositions, and to methods of making and using the same, which are useful to decrease the concentration of, or even substantially eliminate, hydrogen peroxide present in a liquid medium. More particularly, the invention relates to such compositions, and methods for making and using such compositions, useful in destroying residual hydrogen peroxide present in a liquid aqueous medium containing a contact lens which has been disinfected by the action of hydrogen peroxide and preferably cleaned by enzymatic action.

Contact lenses should be periodically cleaned and disinfected by the user to prevent infection or other deleterious effects on ocular health which may be associated with contact lens wear. Currently, there are several different conventional systems and methods which enable the user to clean and disinfect their contact lenses between wearing times. These conventional cleaning and disinfection systems can be divided into "hot" and "cold" systems. Hot systems require the use of heat to disinfect the contact lenses, whereas cold systems use chemical disinfectants at ambient temperatures to disinfect the lenses.

Within the realm of cold disinfection systems are hydrogen peroxide disinfection systems. Disinfecting hydrogen peroxide solutions are effective to kill the bacteria and fungi which may contaminate contact lenses. However, residual hydrogen peroxide on a disinfected contact lens may cause irritation, burning or trauma to the eye unless this hydrogen peroxide is destroyed, i.e., decomposed, neutralized, inactivated or chemically reduced. Therefore, the destruction of the residua hydrogen peroxide in the liquid medium containing the disinfected contact lens is needed to enable safe and comfortable wear of the disinfected contact lens.

Contact lenses can be cleaned by enzymatic action. For example, Huth, et al U.S. Pat. RE. 32,672 discloses the simultaneous cleaning and disinfecting of contact lenses by a method which comprises contacting the lenses with a solution comprising a disinfecting amount of peroxide and an effective amount of peroxide-active proteolytic enzyme for a time sufficient to remove substantially all protein accretions and to disinfect the lenses. This patent further discloses that catalases, organic enzymes which catalyze the degradation of peroxides, can be incorporated into tablets and powders, particularly in time-release form. Both the proteolytic enzyme and the catalase should have high activity to provide a highly effective degree of cleaning and peroxide degradation, respectively.

Associated with the problem of hydrogen peroxide destruction in contact lens disinfection systems are the problems of easy use and user compliance. To enhance user compliance and ease of use, several efforts have focused on one-step disinfection and hydrogen peroxide destruction. In this regard, various time release tablets containing a core tablet and a totally soluble or insoluble coating have been suggested.

Schafer et al European Patent Application 86-109,361.5 discloses a hydrogen peroxide neutralizer tablet covered with a water-soluble coating to delay the dissolution of the tablet. The coating is applied by conventional procedures such as by spraying on a film in coating pans, by fluidized bed methods, or in closed systems. This publication discloses the use of various soluble polymers, such as cellulose ethers, which include suitable polyhydric alcohols to control the timed release as a coating for the neutralizer tablet.

Kaspar et al U.S. Pat. No. 4,568,517 discloses a one step contact lens disinfecting process which involves hydrogen peroxide and a neutralizer having a hydrogen peroxide neutralizing compound in tablet or particle form and a coating encasing the tablet or particles which acts as a delayed release coating. Among the hydrogen peroxide neutralizing compounds disclosed are peroxidase/catalase enzymes. The coating may be made of organically modified cellulose, such as hydroxypropylmethyl cellulose, ethyl cellulose, cellulose acetate phthalate and hydroxypropyl cellulose. The neutralizer can be a coated tablet prepared by spraying an ethanol or acetone solution of the coating material onto a tablet containing the hydrogen peroxide neutralizing compound. The solvent is then evaporated leaving the coating. The use of purely organic solvents tends to produce non-uniform coatings with delayed release characteristics which are not totally satisfactory. In addition, certain organic solvents, such as alcohols, have an adverse effect on the activity of certain of the cleaning enzymes, discussed previously. The use of water as the solvent can have adverse effects on the hydrogen peroxide neutralizing compound, in particular catalase enzyme. It would be advantageous to provide a new solvent system for coating such hydrogen peroxide neutralizing compounds.

There continues to be a need for a one step contact lens disinfecting, and preferably cleaning, system using a hydrogen peroxide destroying component. The delayed release coating on tablets used in such systems should be of sufficient thickness and uniformity to allow enough time for lens disinfecting to take place while, at the same time, allowing release of the hydrogen peroxide destroying component in a reasonable period of time so that the disinfected lens can be safely and comfortably worn.

SUMMARY OF THE INVENTION

New compositions, methods for making such compositions and methods useful for destroying hydrogen peroxide in a liquid aqueous medium, in particular for destroying residual hydrogen peroxide in a liquid aqueous medium containing a disinfected contact lens, have been discovered. The present invention allows the hydrogen peroxide destroying component or components to be initially contacted with the liquid aqueous medium at the same time the contact lens to be disinfected is initially contacted with the liquid aqueous medium. For example, the present compositions and the contact lens to be disinfected can be added to the liquid aqueous medium at substantially the same time. This feature greatly reduces the amount of user time and care required to effectively disinfect his/her lenses and destroy the residual hydrogen peroxide. Better user compliance and a greater degree of user eye safety is provided. The present invention provides a delayed release feature so that the contact lens is effectively disinfected by the action of hydrogen peroxide prior to the release of the hydrogen peroxide destroying component. Further, the present delayed release feature is achieved using a relatively simple and straightforward coating composition which provides for ease in manufacturing the present compositions and decreases the number of potential problems which may result using such compositions. The methods by which the compositions are produced provide delayed release coatings which are highly uniform and, therefore, highly reliable in providing the desired delayed release characteristics. Also, such methods provide the hydrogen peroxide destroying component, in particular catalase, and preferably the cleaning enzyme or enzymes, in a highly active form so that such component or components, and preferably such enzyme or enzymes, are able to perform very effectively.

In one broad aspect, the present invention is directed to a method for producing a hydrogen peroxide destroying composition useful for destroying residual hydrogen peroxide in a hydrogen peroxide-containing liquid aqueous medium, hereinafter referred to as HPLM. This method comprises providing at least one item containing a hydrogen peroxide destroying component, hereinafter referred to as HPDC, effective when released in a HPLM to destroy or cause the destruction of hydrogen peroxide present in the HPLM; applying to the item or items a mixture comprising water, a ketone component and a water soluble coating component in an amount sufficient to coat the item or items with the mixture and form a precoated item or items; and removing at least a portion of the water and ketone component from the precoated item or items. The coated item or items which are formed include a barrier coating containing the water soluble coating component. The barrier coating is structured to delay the release of the HPDC in the HPLM for a period of time after the coated item or items are introduced into the HPLM.

The composition comprising an item and a barrier coating, produced as described above, is new and provides substantial advantages. For example, the combination of water and ketone component as a solvent for the coating component has been found to provide barrier coatings of increased uniformity, e.g., relative to barrier coatings derived using purely organic solvents, which results in compositions having very good delayed release characteristics. In addition, in compositions which include catalase as an HPDC and/or one or more cleaning enzymes, such catalase and/or cleaning enzyme or enzymes have very high or good activity, e.g., increased activity relative to compositions produced by other methods, such as by applying the coating as a mixture of coating component and water or alcohol. In short, the presently useful methods of producing hydrogen peroxide destroying compositions provide new and very effective compositions.

A method for decreasing the concentration of hydrogen peroxide in a HPLM is provided in which a HPLM is contacted with a composition, such as that described herein.

Further, a method of disinfecting a lens, preferably a contact lens, is provided. This method includes contacting a lens to be disinfected with a HPLM at effective lens disinfecting conditions to disinfect the lens. The HPLM is also contacted with a composition, such as that described herein. This composition preferably produces a liquid aqueous medium having no deleterious concentration of hydrogen peroxide. Thus, after the composition has acted, the disinfected contact lens can be removed from the liquid aqueous medium and placed directly in the eye. If, in addition, the contact lens is enzymatically cleaned, it is preferred that the lens be rinsed free of the cleaning enzyme or enzymes before being placed in the eye.

DETAILED DESCRIPTION OF THE INVENTION

The present invention is of value where hydrogen peroxide is used to disinfect all types of lenses, e.g., contact lenses, which are benefited by periodical disinfecting. Such lenses, e.g., conventional contact lenses, in particular soft contact lenses, may be made of any suitable material or combination of materials and may have any suitable configuration not substantially deleteriously affected by hydrogen peroxide, the present compositions or the present methods.

The present invention is particularly useful for destroying residual hydrogen peroxide in a HPLM which has been used to disinfect a contact lens.

The liquid medium used to disinfect a contact lens in the present invention includes a disinfecting amount of hydrogen peroxide. Preferably, a disinfecting amount of hydrogen peroxide means such amount as will reduce the microbial burden by one log in three hours. Still more preferably, the hydrogen peroxide concentration is such that the microbial load is reduced by one log order in one hour. Particularly preferred are those hydrogen peroxide concentrations which reduce the microbial load by one log unit in 10 minutes or less. Relatively mild aqueous hydrogen peroxide solutions, preferably containing about 0.5% to about 6% of hydrogen peroxide (w/v), are known to be effective disinfecting solutions for contact lenses These solutions are effective at killing bacteria and fungi which may be found on contact lenses. However, once contact lens has been disinfected by being immersed in the HPLM, the residual hydrogen peroxide, e.g., on the lens, should be destroyed so that the lens may be safely and comfortably worn on the eye. If this residual hydrogen peroxide is not destroyed before the lens is worn, irritation to the eye or wearing discomfort may occur.

Thus, the present compositions, which are preferably initially contacted with the HPLM at substantially the same time as is the contact lens to be disinfected, allow for effective lens disinfection and, in addition, effectively destroy the residual hydrogen peroxide remaining in the HPLM so that the disinfected lens can be removed from the liquid medium and placed into the eye for safe and comfortable wear. The present composition is preferably present in the form of a tablet, although other forms, such as pills, particles, microgranules, powders and the like, may be employed. The composition preferably includes at least one coated item, for example, a layered tablet, a layered particle, a coated microgranule and the like, each of which includes an item, for example, a core such as a core tablet, and a barrier coating. The barrier coating comprises a water soluble coating component and preferably substantially surrounds the item which includes the HPDC. The item or items are preferably about 40% to about 99% by weight of the total of the item or items plus barrier coating, while the barrier coating is preferably about 1% to about 60% by weight of the total of the item or items plus barrier coating.

Any suitable HPDC may be included in the present compositions. Such HPDCs should effectively destroy the residual hydrogen peroxide and have no undue detrimental effect on the disinfected lens or on the eye into which the disinfected lens is placed. Among the useful HPDCs are hydrogen peroxide reducing agents, enzymes useful to destroy hydrogen peroxide, such as peroxidases and catalase, and mixtures thereof.

Examples of the hydrogen peroxide reducing agents which are useful in the present invention are alkali metal in particular sodium, thiosulfates; thiourea; alkali metal, in particular sodium, sulfites; thioglycerol; N-acetylcysteine alkali metal, in particular sodium, formates; ascorbic acid; isoascorbic acid; glyoxylic acid; pyruvic acid; ophthalmically acceptable salts, such as alkali metal and in particular sodium salts, of such acids; mixtures thereof and the like. A particularly useful HPDC is catalase since it is often effective to substantially eliminate hydrogen peroxide from a liquid medium in a reasonable period of time, for example, on the order of about 1 minute to about 12 hours, preferably about 5 minutes to about 1 hour, after being initially released in the HPLM. One important advantage of the present invention is that the present method of producing the compositions has little or no detrimental effect on the activity of the HPDC, in particular catalase. Thus, relatively reduced amounts of the relatively expensive HPDC can be used to achieve the same hydrogen peroxide destruction and/or the HPDC can more rapidly destroy residual hydrogen peroxide once the HPDC is initially released in the HPLM.

The amount of HPDC employed is preferably sufficient to destroy all the hydrogen peroxide present in the HPLM into which the HPDC is placed. Excess HPDC may be employed. Very large excesses of HPDC are to be avoided since the HPDC itself may cause problems with the disinfected contact lens and/or the ability to safely and comfortably wear such disinfected contact lens. When catalase is employed as a HPDC, it is preferably present in an amount of about 100 to about 1000, more preferably about 150 to about 700, units of catalase activity per milliliter of liquid medium. For example, an especially useful amount of catalase for use in an aqueous solution containing about 3% (w/v) hydrogen peroxide is about 520 units of catalase activity/ml of solution.

The HPDC may be combined with one or more other components, for example, in the at least one item or core of the present compositions. Such other components may include, for example, fillers, binders, tonicity agents, contact lens conditioning/wetting agents, buffering agents, lubricating agents and the like. Each of these components may be present, if at all, in an amount effective to perform its designated function or functions. Examples of each of these types of components are conventional and well known in the art. Therefore, a detailed description of such components is not presented here. An illustrative HPDC-containing core tablet may have the following composition:

| | Wt. % |
|---|---|
| HPDC | 1-30 |
| Filler | 15-90 |
| Tonicity Agent | 1-90 |
| Buffering Agent | 1-50 |
| Lubricating Agent | 0-30 |

Useful tonicity agents include, but are not limited to, sodium chloride, potassium chloride, mannitol, dextrose, glycerin, propylene glycol and mixtures thereof.

Useful contact lens conditioning/wetting agents include, but are not limited to, polyvinyl alcohol, polyoxamers, polyvinylpyrrolidone, hydroxypropylmethyl cellulose and mixtures thereof. Certain of the present coating components may provide one or more other useful functions after being dissolved in the HPLM.

Useful buffering agents include, but not limited to, acetate buffers, citrate buffers, phosphate buffers and borate buffers. Acids and bases may be used to adjust the pH of the present compositions as needed.

Useful lubricating agents include, but are not limited to, polyalkylene glycols, such as polyethylene glycols, preferably having molecular weights in the range of about 500 to about 10,000. Other materials conventionally used as lubricants in ophthalmically acceptable tablets may be employed in the present invention.

The inclusion of one or more of such other components in the present compositions may be important to facilitate the functioning of such compositions and the present methods. For example, it may be desirable to maintain the pH and/or osmolality of the liquid aqueous medium within certain ranges, for example, to obtain preferred enzyme activities, coating component solubility and/or physiological acceptance. One or more of such other components may be included in the mixture which is applied to the item or items and which remain in the coated item or items. Also, such other component or components may be included in the present compositions separate and apart from the coated item or items.

In a useful embodiment, the HPDC is combined with at least one enzyme effective to remove debris from a contact lens. Among the types of debris that form on contact lens during normal use are protein-based debris, mucin-based debris, lipid-based debris and carbohydrate-based debris. One or more types of debris may be present on a single contact lens.

The enzyme employed may be selected from peroxide-active enzymes which are conventionally employed in the enzymatic cleaning of contact lenses. For example, many of the enzymes disclosed in Huth et. al. U.S. Pat. RE 32,672 and Karageozian et al U.S. Pat. No. 3,910,296 are useful in the present invention. Each of these patents is incorporated in its entirety by reference herein. Among the useful enzymes are those selected from proteolytic enzymes, lipases, carbolytic enzymes and mixtures thereof.

Preferred proteolytic enzymes are those which are substantially free of sulfhydryl groups or disulfide bonds, whose presence may react with the active oxygen in the HPLM to the detriment of the activity of the enzyme. Metalloproteases, those enzymes which contain a divalent metal ion such as calcium, magnesium or zinc bound to the protein, may also be used.

A more preferred group of proteolytic enzymes are the serine proteases, particularly those derived from Bacillus and Streptomyces bacteria and Aspergillus molds. Within this grouping, the still more preferred enzymes are the derived alkaline proteases generically called subtilisin enzymes. Reference is made to Deayl, L., Moser, P. W. and Wildi. B. S., "Proteases of the Genus Bacillus. II Alkaline Proteases", Biotechnology and Bioengineering, Vol. XII, pp 213-249 (1970) and Keay, L. and Moser, P. W., "Differentiation of Alkaline Proteases form Bacillus Species" Biochemical and Biophysical Research Comm., Vol 34, No. 5, pp 600-604, (1969).

The subtilisin enzymes are broken down into two subclasses, Subtilisin A and Subtilisin B. In the Subtilisin A grouping are enzymes derived from such species are *B. subtilis, B. licheniformis* and *B. pumilis.* Organisms in this sub-class produce little or no neutral protease or amylase. The Subtilisin B sub-class is made up of enzymes from such organisms a *B. subtilis, B. subtilis var. amylosacchariticus, B. amyloliquefaciens* and *B. subtilis* NRRL B3411 These organisms produce neutral proteases and amylases on a level about comparable to their alkaline protease production. One or more enzymes from the Subtilisin A sub-class are particularly useful.

In addition, other preferred enzymes are, for example, pancreatin, trypsin, collaginase, keratinase, carboxylase, aminopeptidase, elastase, and aspergillo-peptidase A and B, pronase E (from *S. griseus*) and dispase (from *Bacillus polymyxa*).

An effective amount of enzyme is to be used in the practice of this invention. Such amount will be that amount which effects removal in a reasonable time (for example overnight) of substantially all of at least one type of debris from a lens due to normal wear. This standard is stated with reference to contact lens wearers with a history of normal pattern of lens debris accretion, not the very small group who may at one time or another have a significantly increased rate of debris accretion such that cleaning is recommended every day, or every two or three days.

The amount of enzyme required to make an effective cleaner will depend on several factors, including the inherent activity of the enzyme, and the extent of its interaction with the hydrogen peroxide present.

As a basic yardstick, the working solution should contain sufficient enzyme to provide about 0.001 to about 3 Anson units of activity, preferably about 0.002 to about 1 Anson units, per single lens treatment. Higher or lower amounts may be used.

Enzyme activity is pH dependent so for any given enzyme, there is a particular pH range in which that enzyme will function best. The determination of such range can readily be done by known techniques.

The HPDC-containing item or items are provided with a delayed release coating, a barrier coating. The present barrier coating can be formulated and applied so that the amount of time after the composition is introduced into the HPLM but before any HPDC is released in the HPLM is very effectively controlled. After this period of time, the barrier coating is dissolved into the HPLM sufficiently to rapidly release HPDC, preferably sufficient HPDC to destroy substantially all the remaining or residual hydrogen peroxide in the HPLM. The present compositions are preferably formulated and structured to delay the release of the HPDC in the HPLM for a time sufficient to effectively disinfect a contact lens and then release the HPDC in the HPLM for rapid and predictable destruction of the residual hydrogen peroxide.

The present delayed release coating or barrier coating is derived from a mixture comprising water, a ketone component and a water soluble coating component. This mixture is applied to the HPDC-containing item or items in an amount sufficient to coat the item or items, in particular substantially all of the item or items, and form a precoated item or items. At least portions of the water and ketone component are removed from the precoated item or items to form the coated item or items, the item or items with a barrier coating.

The water soluble coating components useful in the present invention include those coating components which dissolve in water over a period of time. The coating component or components chosen for use should have no substantial detrimental effect on the lens being treated, on the disinfecting and cleaning of the lens, or on the person in whose eye the disinfected/cleaned lens is to be placed. The coating component or components used in the present barrier coatings and the amount or thickness of the barrier coating are preferably chosen so that the barrier coating dissolves into the HPLM at a rate so that the HPDC is released in the HPLM after a period of time sufficient for the hydrogen peroxide to disinfect the lens located in the HPLM.

The water soluble coating component or components may be chosen from ophthalmically acceptable materials, preferably polymeric materials, which function as described herein. Particularly useful coating components include water soluble cellulose derivatives, water soluble methacrylate-based polymers, water soluble vinyl pyrrolidone-based polymers and mixtures thereof. Mixed polymers of methyl vinyl ether and maleic acid anhydride, and polyvinyl alcohols can also be used.

The water soluble methacrylate-based polymers include polymers derived from methacrylic acid and/or methacrylic acid esters. Water soluble vinyl pyrrolidone-based polymers useful in the present invention include polymers derived in whole or in part from vinyl pyrrolidone, such as polyvinylpyrrolidone, polyvinylpyrrolidone derivatives, such as ethers and esters, and mixtures thereof. A specific example of useful water soluble vinyl pyrrolidone-based polymers is polyvinylpyrrolidone acetate, such as the product sold by BASF under the trademark Kollidon VA-64. Water soluble methacrylate-based polymers, water soluble vinyl pyrrolidone polymers and mixtures thereof are quite useful, particularly in forming coatings which contain one or more of the presently useful cleaning enzymes. Such coatings are frequently thin and/or rapidly solubilized in the HPLM so as to release the cleaning enzyme or enzymes in the HPLM shortly after the composition is first contacted with the HPLM to clean the lens while it is being disinfected by the action of hydrogen peroxide. This simultaneous cleaning/disinfecting of the contact lens reduces the overall lens treating time and can act to promote the degree of cleaning achieved.

The more preferred water soluble coating components comprise at least one water soluble cellulose derivative.

The water soluble cellulose derivatives useful in the present invention can be obtained by derivatizing cellulose to achieve the desired degree of water solubility. Substituent groups selected from hydrocarbyl groups and substituted hydrocarbyl groups are particularly useful for inclusion in the present cellulose derivatives. Such substituents which include 1 to about 10 carbon atoms, and such groups which include a polar group, such as a hydroxyl group, a carbonyl group, a carboxyl group and the like, are very effective in providing cellulose derivatives with the desired water solubility. Such water soluble cellulose derivatives can be produced using conventional and well known organic synthesis techniques.

In one embodiment, the water soluble cellulose derivatives are selected from water soluble cellulose ethers, water soluble cellulose esters and mixtures thereof, preferably water soluble cellulose ethers and mixtures thereof. Examples of water soluble cellulose esters include cellulose acetate phthalate, hydroxypropylmethyl cellulose phthalate and the like.

Water soluble alkyl ethers and/or hydroxyalkyl ethers of cellulose are among the water soluble cellulose ethers which can be employed. The alkyl groups preferably have 1 to about 6, more preferably 1 to about 3 or 4, carbon atoms. Specific examples of useful water soluble cellulose ethers include hydroxypropylmethyl cellulose, ethyl cellulose, methyl cellulose, hydroxyethylmethyl cellulose, hydroxypropyl cellulose, hydroxyethyl cellulose, metal, in particular alkali metal, salts of cellulose ethers such as sodium carboxymethyl cellulose, and the like and mixtures thereof. A particularly useful water soluble cellulose derivative is hydroxypropylmethyl cellulose.

The ketone component or components useful in the present invention are chosen to provide effective barrier coatings and to have no substantial adverse effect on the activity of the HPDC, in particular catalase, or on the activity of the cleaning enzyme or enzymes, if any, present in the present composition. The ketone component or components have the characteristic ketone structure and are preferably selected from ketones having 3 to about 6 carbon atoms per molecule. The ketone component or components may include one or more substituent groups provided that such group or groups do not substantially interfere with the functioning of the ketone component or components in the present invention. Specific examples of useful ketone components include acetone, methyl ethyl ketone, methyl isobutyl ketone and the like and mixtures thereof.

The relative amounts of water, ketone component, and water soluble coating component employed in the present invention are preferably selected to achieve effective barrier coatings with little or no degradation in the activity of the HPDC, and cleaning enzyme or enzymes, if present. More preferably, water is present in the mixture in a minor amount, i.e., less than about 50% (v/v), and the ketone component is present in the mixture in a major amount, i.e., more than about 50% (v/v), of the total amount of water and ketone component present in the mixture. Relatively high concentrations of water have been found to have a detrimental effect on the activity of the HPDC, in particular catalase, in the item or items. For this reason, it is still more preferred to include no more than about 20% (v/v) of water in the mixture. Coated items produced from mixtures without water tend to have less uniform barrier coatings and to have less reliable and predictable delayed release characteristics.

The amount of water soluble coating component included in the mixture is such as to form a barrier coating on the item or items with the desired delayed release characteristics. Preferably, the amount of such coating component is such as to be completely solubilized in the mixture. In one embodiment, the amount of coating component present in the mixture is in the range of about 0.1% to about 20%, preferably about 0.2% to about 10% and more preferably about 0.5% to about 5%, (w/v) of the total mixture.

A particularly useful mixture includes 3% (w/v) of hydroxypropylmethyl cellulose in a liquid medium of 90% (v/v) of acetone and 10% (v/v) of water.

The mixture may include one or more other components which act, for example, to facilitate applying the mixture to the item or items, to facilitate removing water and/or ketone component or components from the precoated core, and/or to provide a barrier coating with one or more useful properties and/or components which are useful to treat the lens when released in the HPLM. For example, the mixture may include one or more lubricating agents and/or deposit prevention agents to assist in maintaining the integrity of the barrier coating and to reduce deposit formation in the liquid aqueous medium in which the composition is used.

In a particularly useful embodiment, one or more cleaning enzymes, as described above, are included in the mixture so that the barrier coating includes an amount of such enzyme or enzymes effective to remove at least one type of debris from a contact lens when released into the HPLM. Particularly useful enzymes for this embodiment of the present invention are peroxide-active proteolytic enzymes, such as those described in Huth et al U.S. Pat. RE 32,672. Subtilisin A is an especially useful cleaning enzyme for inclusion in the present mixture and barrier coating.

Alternately, the coated item or items can be further coated with a cleaning enzyme-containing outer coating to form an outer coated item or outer coated items structured to release the cleaning enzyme in the HPLM relatively shortly after, or even substantially at the same time as, the outer coated item or items are initially contacted with the HPLM. In this embodiment, the cleaning enzyme is located separate and apart from the main barrier coating of the composition. The outer coating can be derived by combining the cleaning enzyme with the presently useful mixture, applying this material to the coated item or items and removing at least a portion of the water and ketone component or components. The cleaning enzyme can be applied to the coated item or items by itself or together with a material other than the presently useful water soluble coating components. For example, other water soluble materials may be combined with the cleaning enzyme and applied to the coated item or items to form the outer coated item or items. However, in one useful embodiment, the cleaning enzyme is applied to the coated item or items as a mixture comprising water, a ketone component, the cleaning enzyme or enzymes and one or more of the presently useful coating components, more preferably chosen from methacrylate-based polymers, vinyl pyrrolidone-based polymers and mixtures thereof. In certain instances, e.g., where the coating component is relatively hydroscopic, a final protective coating, for example, comprising one or more water soluble cellulose derivatives, may be applied to the coated or outer coated item or items, in particular using the method of the present invention, to protect the coated or outer coated item or items, such as during storage. This protective coating, which is often relatively thin, dissolves into the liquid aqueous medium very quickly, preferably substantially immediately, after the protected item or items are first contacted with the liquid aqueous medium.

The mixture, preferably a liquid solution, can be applied to the item or items employing any conventional technique used, for example, to apply a liquid precursor of a delayed release coating to an item, such as a tablet, pill, microgranule, powder and the like. For example, the mixture can be sprayed onto the item or items. Alternately, the item or items can be dipped into the mixture. Conventional fluidized bed techniques can also be used. In any event, such applying step is effective to produce or form a precoated item or items.

The precoated item or items are subjected to conditions effective to remove, e.g., evaporate, at least a portion of the water and ketone component from the precoated item or items and form the coated item or coated items. Such conditions include, for example, ambient or slightly elevated temperatures.

In instances in which the final product, e.g., tablet, is to include a plurality of coated or outer coated items, conventional tabletting techniques, in particular compressive tabletting techniques, can be employed to form the final product. For example, a plurality of coated and/or outer coated items, in the form of microgranules, can be included in a final product tablet using a conventional compressive tablet press. One or more conventional tabletting components, e.g., fillers, bulking agents, lubricants and the like, as well as one or more of the other components noted previously can be included in the final product tablet. In addition, one or more cleaning enzymes, such as described herein, may be included separate and apart from the present coated or outer coated items, for example, with the conventional tabletting and other components. When the final product tablet is introduced into the liquid aqueous medium, e.g., a HPLM, the cleaning enzyme or enzymes are very quickly released, to clean the contact lens in the liquid aqueous medium of debris, while the barrier coating on the coated or outer coated items delays the release of the HPDC. This embodiment is particularly effective when coated items including no cleaning enzyme or enzymes are used. The use of a final product tablet including a plurality of coated items, e.g., microgranules, eliminates the need to coat the final product tablet as a whole, and very effectively provides for simultaneous enzymatic cleaning and hydrogen peroxide disinfecting of contact lenses.

The present method of disinfecting a lens, preferably a contact lens, includes contacting the lens to be disinfected with a HPLM at effective lens disinfecting conditions. The HPLM is contacted with a composition which includes a coated item or items containing a HPDC and a barrier coating, such as described herein. Using this method, the lens is disinfected and the residual hydrogen peroxide in the HPLM is effectively destroyed. Thus, after the HPDC has been released in the HPLM and acts to effectively destroy the residual hydrogen peroxide, the lens can be safely and comfortably taken directly from the liquid medium in which it was disinfected. If, as is preferred, the contact lens is enzymatically cleaned in addition to being disinfected, the cleaned/disinfected lens is preferably rinsed free of the cleaning enzyme or enzymes before being placed in the eye.

In a particularly useful embodiment, the contact lens to be disinfected is placed into the HPLM at substantially the same time as in the present composition. After a predetermined period of time, during which the contact lens is disinfected, the HPDC is released in the HPLM and effectively destroys the residual hydrogen peroxide.

In the event that a debris removing or cleaning enzyme is present in the composition, the contact lens in the liquid medium is also effectively cleaned of at least one type of debris. This cleaning action can occur either at the time the lens is being disinfected, e.g., if the enzyme is released in the HPLM when the composition is initially contacted with the HPLM or shortly thereafter or before the HPDC is released in the HPLM; or after the lens is disinfected, e.g., if the enzyme is released into the HPLM when the HPDC is released in the HPLM or thereafter. Preferably, the lens is cleaned at the time it is being disinfected.

It is preferred that the HPDC not be released in the HPLM until the lens has been immersed in the HPLM for a time sufficient, more preferably in the range of about 1 minute to about 4 hours and still more preferably in the range of about 5 minutes to about 1 hour, to effectively disinfect the lens. It is also preferred that substantially all of the residual hydrogen peroxide in the HPLM be destroyed in less than about 3 hours, more preferably in less than about 1 hour and still more preferably in less than about 30 minutes, after the HPDC is initially released into the HPLM.

The disinfecting contacting preferably occurs at a temperature to maintain the liquid medium substantially liquid. For example, when the liquid medium is aqueous-based, it is preferred that the contacting temperature be in the range of about 0° C. to about 100° C., and more preferably in the range of about 10° C. to about 60° C. and still more preferably in the range of about 15° C. to about 30° C. Contacting at or about ambient temperature is very convenient and useful. The contacting preferably occurs at or about atmospheric pressure. This contacting preferably occurs for a time to substantially completely disinfect the lens being treated. Such contacting times can be in the range of about 1 minute to about 12 hours or more.

The following non-limiting examples illustrate certain aspects of the present invention.

EXAMPLE 1

A two layer tablet, having a core tablet surrounded by a coating was prepared for testing. The core tablet and coating had the following compositions:

| CORE TABLET | |
|---|---|
| Crystalline catalase[1] | 1.5 mg |
| Sodium chloride | 89.4 mg |
| Dibasic sodium phosphate (anhydrous) | 12.5 mg |
| Monobasic sodium phosphate monohydrate | 0.87 mg |
| Polyethylene glycol (molecular weight of about 3350) | 1.05 mg |
| COATING | 3 to 6 mg |
| Hydroxypropylmethyl cellulose | |

[1]The amount of catalase added was determined by an assay of the batch of product to be used. The tablet prepared contained about 5200 units of catalase activity.

The coating was applied to the core tablet as follows. The hydroxypropylmethyl cellulose was dissolved in a liquid vehicle containing 90% (v/v) acetone and 10% (v/v) water. The final formulation included 3% (w/v) hydroxypropylmethyl cellulose. Using a Glatt fluidized bed/air suspension coater, the core tablet was coated with the final formulation. After drying to remove water and acetone, the layered or coated tablet included sufficient hydroxypropylmethyl cellulose to provide the desired delayed release characteristics without unduly adversely affecting, e.g., deactivating, the catalase in the core.

A series of twenty (20) layered tablets prepared as described above were tested to determine their effectiveness in destroying hydrogen peroxide. This test was conducted as follows. 10 ml of a 3% (w/v) aqueous solution of hydrogen peroxide was provided at room temperature. The layered tablet was introduced into the solution and periodic measurements of the amount of oxygen released from the solution were made. The amount of oxygen released was used to determine the hydrogen peroxide concentration remaining in the solution.

Results of these tests were as follows:

| Time After Tablet Introduced Into Solution, min | Range of Peroxide Concentrations In Solution for Twenty (20) Tablets, % w/v |
| --- | --- |
| 0 | 3.0 |
| 5 | 2.85–3.0 |
| 10 | 2.7–2.95 |
| 20 | 2.1–2.8 |
| 25 | 1.0–2.4 |
| 30 | 0.1–1.7 |
| 35 | 0.0–1.0 |
| 40 | 0.0–0.6 |
| 45 | 0.0–0.2 |

These results demonstrate that the coating effectively delays the release of the catalase for a time sufficient to allow the action of the hydrogen peroxide in the aqueous solution to effectively disinfect a contact lens which is introduced into the solution at the same time as the layered tablet is introduced. Further, these results demonstrate that the hydrogen peroxide in the solution can be substantially completely destroyed by the catalase very quickly and very completely after release of the catalase so that a disinfected contact lens can be removed from this solution and placed directly onto a human eye for safe and comfortable wear.

EXAMPLE 2

A three layer tablet, having a core tablet surrounded by two coating layers was prepared for testing. The core tablet had the following compositions:

| CORE TABLET | |
| --- | --- |
| Crystalline catalase[1] | 1.5 mg |
| Sodium chloride | 89.4 mg |
| Dibasic sodium phosphate (anhydrous) | 12.5 mg |
| Monobasic sodium phosphate monohydrate | 0.87 mg |
| Polyethylene glycol (molecular weight of about 3350) | 1.05 mg |
| COATING Hydroxypropylmethyl cellulose | 3 to 6 mg |

[1]The amount of catalase added was determined by an assay of the batch of product to be used. The tablet prepared contained about 5200 units of catalyst activity.

The coating was applied to the core tablet as follows. The first spraying formulation was derived by dissolving hydroxypropylmethyl cellulose in a liquid vehicle containing 85% (v/v) acetone and 15% (v/v) water. This first spraying composition included 3% (w/v) hydroxypropylmethyl cellulose. The second spraying formulation was derived by dissolving hydroxypropylmethyl cellulose and Subtilisin A enzyme in the above-noted liquid vehicle. This second spraying formulation included 3% (w/v) hydroxypropylmethyl cellulose and 0.05 to 0.1 units/ml Subtilisin A enzyme. Using a Glatt fluidized bed/air suspension coater, the core tablet was coated with the first formulation. After drying, the two layered tablet was sprayed with the second formulation using the above-noted system. After drying, the three (3) layer tablet included sufficient Subtilisin A enzyme to clean a contact lens of proteinaceous debris, and sufficient hydroxypropylmethyl cellulose to provide the desired delayed release characteristics without unduly adversely affecting, e.g., deactivating, the catalase in the core.

A series of twenty (20) layered tablets prepared as described above were tested to determine their effectiveness in destroying hydrogen peroxide. This test was conducted as follows. 10 ml of a 3% (w/v) aqueous solution of hydrogen peroxide was provided at room temperature. The layered tablet was introduced into the solution and periodic measurements of the amount of oxygen released from the solution were made. The amount of oxygen released was used to determine the hydrogen peroxide concentration remaining in the solution.

Results of these tests were as follows:

| Time After Tablet Introduced Into Solution, min | Range of Peroxide Concentrations In Solution for Twenty (20) Tablets, % w/v |
| --- | --- |
| 0 | 3.0 |
| 5 | 2.85–3.0 |
| 10 | 2.7–2.95 |
| 20 | 2.1–2.8 |
| 25 | 1.0–2.4 |
| 30 | 0.1–1.7 |
| 35 | 0.0–1.0 |
| 40 | 0.0–0.6 |
| 45 | 0.0–0.2 |

These results demonstrate that the coating effectively delays the release of the catalase for a time sufficient to allow the action of the hydrogen peroxide in the aqueous solution to effectively disinfect a contact lens which is introduced into the solution at the same time as the layered tablet is introduced. Further, these results demonstrate that the hydrogen peroxide in the solution can be substantially completely destroyed by the catalase very quickly and very completely after release of the catalase so that a disinfected contact lens can be removed from this solution and placed directly onto a human eye for safe and comfortable wear.

EXAMPLE 3

A layered tablet in accordance with Example 1 is used to disinfect a conventional soft contact lens as follows. 10 ml of a 3% (w/v) aqueous solution of hydrogen peroxide is provided at room temperature. The contact lens to be disinfected and the layered tablet are placed in the solution at the same time. For approximately ten (10) minutes, the solution remains substantially quiet, i.e., substantially no bubbling (gas evolution) takes place. For the next approximately 20 to 25 minutes, the solution bubbles. After this period of time, the solution becomes and remains quiet. One hour after the contact lens is first introduced into the solution, it is removed from the solution and placed directly into the wearer's eye. It is found that after one hour, the contact lens is effectively disinfected. Also, the lens wearer experiences no discomfort or eye irritation from wearing the disinfected contact lens. The bubbling of the solution provides a indication that hydrogen peroxide destruction is occurring. An indication that the peroxide destruction is complete is provided when the bubbling stops.

EXAMPLE 4

A layered tablet in accordance with Example 2 is used to disinfect and clean a protein-based debris laden soft contact lens as follows. 10 ml of a 3% (w/v) aqueous solution of hydrogen peroxide is provided at room temperature. The contact lens to be disinfected and cleaned and the enzyme-containing layered tablet are placed in the solution at the same time. For approximately ten (10) minutes the solution remains substantially quiet. For the next approximately 20 to 25 minutes, the solution bubbles. After this period of time, the solution becomes and remains quiet. One hour after the contact lens is first introduced into the solution, it is removed from the solution, rinsed with physiological saline solution to remove the subtilisin A and placed into the wearer's eye. It is found that after one hour, the contact lens is effectively disinfected and cleaned of protein-based debris. The lens wearer experiences no discomfort or eye irritation from wearing the disinfected and cleaned contact lens.

EXAMPLE 5

A direct compression tablet containing coated microgranules including catalase is prepared as follows:

Microgranules composed of sodium chloride, sucrose and catalase are prepared, using conventional granulation techniques. The weight ratio of sodium chloride to sucrose in the microgranules is 110 to 1. The microgranules include about 60 units of catalase per milligram of sodium chloride plus sucrose.

Hydroxypropylmethyl cellulose is dissolved in a liquid vehicle containing 90% (v/v) acetone and 10% (v/v) water. The final formulation contains 3% (w/v) hydroxypropylmethyl cellulose. This formulation is sprayed onto the microgranules and coats the microgranules. After drying to remove water and acetone, the final coated microgranules include a coating of hydroxypropylmethyl cellulose in an amount sufficient to provide the desired delayed release characteristics without unduly adversely affecting, e.g., deactivating, the catalase in the core microgranules. The coated microgranules include about 5% by weight of hydroxypropylmethyl cellulose.

The direct compression tablet has the following composition:

| | |
|---|---|
| Coated microgranules | 44 mg |
| Sodium chloride | 48 mg |
| Dibasic sodium phosphate (anhydrous) | 12.5 mg |
| Monobasic sodium phosphate (monohydrate) | 0.87 mg |
| Polyethylene glycol (molecular weight of about 3350) | 1.05 mg |

These components are combined and mixed. The resulting mixture is processed in a conventional tablet press to form the final direct compression tablet.

EXAMPLE 6

The direct compression tablet prepared as in Example 5 is used to disinfect a conventional soft contact lens as follows. 10 ml of a 3% (w/v) aqueous solution of hydrogen peroxide is provided at room temperature. The contact lens to be disinfected and the direct compression tablet are placed in the solution at the same time. For approximately ten (10) minutes, the solution remains substantially quiet, i.e., substantially no bubbling (gas evolution) takes place. For the next approximately 20 to 25 minutes, the solution bubbles. After this period of time, the solution becomes and remains quiet. One hour after the contact lens is first introduced into the solution, it is removed from the solution and placed directly into the wearer's eye. It is found that after one hour, the contact lens is effectively disinfected. Also, the lens wearer experiences no discomfort or eye irritation from wearing the disinfected contact lens. The bubbling of the solution provides a indication that hydrogen peroxide destruction is occurring. An indication that the peroxide destruction is complete is provided when the bubbling stops.

EXAMPLE 7

Example 5 is repeated except that the direct compression tablet included 0.03 units of Subtilisin A (0.1 mg). This proteolytic enzyme is added to the mixture as a powder before tabletting.

EXAMPLE 8

The direct compression tablet prepared as in Example 7 is used to disinfect and clean a protein-based debris laden soft contact lens as follows. 10 ml of a 3% (w/v) aqueous solution of hydrogen peroxide is provided at room temperature. The contact lens to be disinfected and cleaned and the enzyme-containing direct compression tablet are placed in the solution at the same time. For approximately ten (10) minutes the solution remains substantially quiet. For the next approximately 20 to 25 minutes, the solution bubbles. After this period of time, the solution becomes and remains quiet. One hour after the contact lens is first introduced into the solution, it is removed from the solution, rinsed with physiological saline solution to remove the subtilisin A and placed into the wearer's eye. It is found that after one hour, the contact lens is effectively disinfected and cleaned of protein-based debris. The lens wearer experiences no discomfort or eye irritation from wearing the disinfected and cleaned contact lens.

EXAMPLE 9

Example 2 is repeated except that the second spraying formulation is derived by dissolving polyvinylpyrrolidone acetate (sold by BASF under the trademark Kollidon VA-64) and Subtilisin A in a liquid vehicle containing 85% (v/v) acetone and 15% (v/v) water. After drying, the three (3) layer tablet includes 1 to 2 mg polyvinylpyrrolidone acetate and about 0.003 units of Subtilisin A enzyme, sufficient to clean a contact lens of proteinaceous debris. This tablet also includes sufficient hydroxypropylmethyl cellulose to provide the desired delayed release characteristics without unduly adversely affecting, e.g., deactivating, the catalase in the core.

EXAMPLE 10

Example 4 is repeated except that the layered tablet prepared in Example 9 is used instead of the tablet in accordance with Example 2. It is found that after one hour, the contact lens is effectively disinfected and cleaned of protein-based debris. The lens wearer experiences no discomfort or eye irritation from wearing the disinfected and cleaned contact lens.

EXAMPLE 11

Example 9 is repeated except that the three (3) layer tablet is further coated with a small amount of hydroxypropylmethyl cellulose, as a finishing coat. A third spraying formulation is derived by dissolving hydroxypropylmethyl cellulose in a liquid vehicle containing 85% (v/v) acetone and 15% (v/v) water. Using a Glatt fluidized bed/air suspension coater, the three (3) layer tablet is coated with the third spraying formulation. After drying, the resulting four (4) layer tablet has substantially all the attributes of the three (3) layer tablet of Example 9. In addition, the outer coating of hydroxypropylmethyl cellulose acts to protect the inner portions of the tablet, e.g., from moisture. This protective outer layer is particularly useful when the third layer includes a somewhat hydroscopic material, such a polyvinylpyrrolidone acetate.

EXAMPLE 12

Example 4 is repeated except that the layered tablet prepared in Example 11 is used instead of the tablet in accordance with Example 2. It is found that after one hour, the contact lens is effectively disinfected and cleaned of protein-based debris. The lens wearer experiences no discomfort or eye irritation from wearing the disinfected and cleaned contact lens.

While this invention has been described with respect to various specific examples and embodiments, it is to be understood that the invention is not limited thereto and that it can be variously practiced within the scope of the following claims.

What is claimed is:

1. A method for producing a hydrogen peroxide destroying composition useful for destroying residual hydrogen peroxide in a hydrogen peroxide-containing liquid aqueous medium comprising:
   providing an item containing a hydrogen peroxide destroying component effective when released in a hydrogen peroxide-containing liquid aqueous medium to destroy or cause the destruction of hydrogen peroxide present in the hydrogen peroxide-containing liquid aqueous medium; and
   applying to said item a mixture comprising water, a ketone component and a water soluble coating component in an amount sufficient to coat substantially all of said item with said mixture and form a precoated item; and
   removing water and said ketone component from said precoated item and forming a coated item which includes a coating containing said water soluble coating component and is structured to delay the release of said hydrogen peroxide destroying component in the hydrogen peroxide-containing liquid aqueous medium for a period of time after said coated item is introduced into the hydrogen peroxide-containing liquid aqueous medium.

2. The method of claim 1 wherein said mixture comprises a liquid containing a minor amount by volume of water and a major amount by volume of said ketone component based on the total of water and said ketone component present in said mixture, and said water soluble coating component is selected form the group consisting of water soluble cellulose derivatives, water soluble methacrylate-based polymers, water soluble vinyl pyrrolidone-based polymers and mixtures thereof.

3. The method of claim 1 wherein said ketone component has up to about 6 carbon atoms per molecule and said water soluble coating component is selected from the group consisting of water soluble cellulose ethers, water soluble cellulose esters and mixtures thereof.

4. The method of claim 1 wherein said ketone component is acetone and said water soluble coating component is hydroxypropylmethyl cellulose.

5. The method of claim 1 wherein said hydrogen peroxide destroying component comprises catalase and said mixture comprises about 20% or less by volume of water.

6. The method of claim 1 wherein said mixture further comprises an enzyme capable of removing debris from a contact lens located in the hydrogen peroxide-containing liquid aqueous medium, said coated item includes said enzyme.

7. The method of claim 6 wherein said coated item is structured to release said enzyme in the hydrogen peroxide-containing liquid aqueous medium before said hydrogen peroxide destroying component is released in the hydrogen peroxide-containing liquid aqueous medium.

8. The method of claim 7 wherein said enzyme is Subtilisin A, said hydrogen peroxide destroying component comprises catalase, said water soluble coating component is hydroxypropylmethyl cellulose, said ketone component is acetone and said mixture comprises about 20% or less by volume of water.

9. The method of claim 8 which further comprises:
   combining a plurality of said coated items and an enzyme capable of removing debris from a contact lens located in the hydrogen peroxide-containing liquid aqueous medium to form a combination; and
   forming a tablet from said combination.

10. The method of claim 1 which further comprises:
    applying to said coated item a second mixture comprising water, a second ketone component, a second water soluble coating component and an enzyme capable of removing debris from a contact lens located in the hydrogen peroxide-containing liquid aqueous medium to coat substantially all of said coated item with said second mixture and form a second precoated item; and
    removing water and said second ketone component from said second precoated item and forming a second coated item which includes a second coating containing said second coating component and said enzyme, said second coated item being structured to release said enzyme in the hydrogen peroxide-containing liquid aqueous medium before said hydrogen peroxide destroying component is released in the hydrogen peroxide-containing liquid aqueous medium.

11. The method of claim 10 wherein said second mixture comprises a liquid containing a minor amount by volume of water and a major amount by volume of said second ketone component based on the total of water and said second ketone component present in said second mixture, and said second water soluble coating component is selected form the group consisting of water soluble cellulose derivatives, water soluble methacrylate-based polymers, water soluble vinyl pyrrolidone-based polymers and mixtures thereof.

12. The method of claim 10 wherein said hydrogen peroxide destroying component comprises catalase.

13. The method of claim 10 wherein said enzyme is Subtilisin A, said hydrogen peroxide destroying component comprises catalase, said second water soluble coating component is hydroxypropylmethyl cellulose, said second ketone component is acetone and said second mixture comprises about 20% or less by volume of water.

14. The method of claim 1 which further comprises:
    combining a plurality of said coated items and an enzyme capable of removing debris from a contact lens located in the hydrogen peroxide-containing liquid aqueous medium to form a combination; and
    forming a tablet from said combination.

15. A composition comprising an item containing a hydrogen peroxide destroying component effective when released in a liquid aqueous medium to destroy or cause the destruction of hydrogen peroxide present in the liquid aqueous medium, and a barrier coating located on said item and acting to substantially prevent the release of said hydrogen peroxide destroying component for a period of time after said composition is initially contacted with a hydrogen peroxide-containing liquid aqueous medium, said barrier coating comprising a water soluble coating component and being derived from a mixture comprising water, a ketone component and said water soluble coating component, which mixture is applied to said item.

16. The composition of claim 15 wherein said mixture comprises a liquid comprising a minor amount by volume of water and a major amount by volume of said ketone component based on the total of water and said ketone component present in said mixture, and said water soluble coating component is selected from the group consisting of water soluble cellulose derivatives, water soluble methacrylate-based polymers, water soluble vinyl pyrrolidone-based polymers and mixtures thereof.

17. The composition of claim 15 wherein said ketone component has up to about 6 carbon atoms per molecule and said water soluble coating component is selected from the group consisting of water soluble cellulose ethers, water soluble cellulose esters and mixtures thereof.

18. The composition of claim 15 wherein said ketone component is acetone and said water soluble coating component is hydroxypropylmethyl cellulose.

19. The composition of claim 15 wherein said hydrogen peroxide destroying component comprises catalase and said mixture comprises about 20% or less by volume of water.

20. The composition of claim 15 which further comprises an enzyme capable of removing debris from a contact lens located in the liquid aqueous medium, said composition including an effective amount of said enzyme to substantially remove at least one type of debris from a debris laden contact lens located in the liquid aqueous medium in which said enzyme is released.

21. The composition of claim 20 wherein said enzyme is Subtilisin A, said hydrogen peroxide destroying component comprises catalase, said water soluble coating component is hydroxypropylmethyl cellulose, said ketone component is acetone and said mixture comprises about 20% or less by volume of water.

22. The composition of claim 20 which has a layered structure with said item being substantially coated with a first coating comprising said water soluble coating component to form a first coated item which is substantially coated with a second coating comprising a second water soluble coating component and said enzyme.

23. The composition of claim 22 wherein said hydrogen peroxide destroying component comprises catalase.

24. The composition of claim 22 wherein said enzyme is Subtilisin A, said hydrogen peroxide destroying component comprises catalase, and said water soluble coating component includes hydroxypropylmethyl cellulose.

25. The composition of claim 20 which is in the form of a tablet including a plurality of said items with said barrier coating located thereon.

26. The composition of claim 25 wherein said hydrogen peroxide destroying component comprises catalase.

27. The composition of claim 25 wherein said enzyme is Subtilisin A, said hydrogen peroxide destroying component comprises catalase, and said water soluble coating component includes hydroxypropylmethyl cellulose.

28. A method of disinfecting a lens comprising:
contacting a lens to be disinfected with a hydrogen peroxide-containing liquid aqueous medium at effective lens disinfecting conditions, thereby disinfecting said lens; and
contacting said hydrogen peroxide-containing aqueous liquid medium with a composition comprising an item containing a hydrogen peroxide destroying component effective when released in a liquid aqueous medium to destroy or cause the destruction of hydrogen peroxide present in the liquid aqueous medium, and a barrier coating located on said item and acting to substantially prevent the release of said hydrogen peroxide destroying component for a period of time after said composition is initially contacted with said hydrogen peroxide-containing liquid aqueous medium, said barrier coating comprising a water soluble coating component and being derived from a mixture comprising water, a ketone component and said water soluble coating component, which mixture is applied to said item.

29. The method of claim 28 wherein said mixture comprises a liquid containing a minor amount by volume of water and a major amount by volume of said ketone component based on the total of water and said ketone component present in said mixture, and said water soluble coating component is selected from the group consisting of water soluble cellulose derivatives, water soluble methacrylate-based polymers, water soluble vinyl pyrrolidone-based polymers and mixtures thereof.

30. The method of claim 28 wherein said composition further comprises an enzyme capable of removing debris from a contact lens located in said hydrogen peroxide-containing liquid aqueous medium, said composition being structured to release said enzyme in said hydrogen peroxide-containing liquid aqueous medium before said hydrogen peroxide destroying component is released in said hydrogen peroxide-containing liquid aqueous medium.

* * * * *